US009233176B2

(12) United States Patent
Lawaczek et al.

(10) Patent No.: US 9,233,176 B2
(45) Date of Patent: Jan. 12, 2016

(54) SYSTEMS AND METHOD OF DELIVERING FLUIDS TO A PATIENT OF VARYING CONCENTRATION

(75) Inventors: Ruediger Lawaczek, Berlin (DE); John F. Kalafut, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 1184 days.

(21) Appl. No.: 12/302,907

(22) PCT Filed: Jun. 6, 2007

(86) PCT No.: PCT/US2007/070497
§ 371 (c)(1),
(2), (4) Date: Dec. 1, 2008

(87) PCT Pub. No.: WO2007/143682
PCT Pub. Date: Dec. 13, 2007

(65) Prior Publication Data
US 2009/0240142 A1  Sep. 24, 2009

Related U.S. Application Data

(60) Provisional application No. 60/804,011, filed on Jun. 6, 2006.

(51) Int. Cl.
*A61K 49/18* (2006.01)
*A61M 5/00* (2006.01)
(Continued)

(52) U.S. Cl.
CPC .............. *A61K 49/18* (2013.01); *A61K 49/0447* (2013.01); *A61M 5/007* (2013.01); *A61M 31/005* (2013.01)

(58) Field of Classification Search
CPC .............. A61K 49/18; A61K 49/0447; A61K 49/0002; A61K 49/00; A61B 8/481; A61B 6/484; A61M 5/007; A61M 31/005
USPC ................... 600/420, 430–435; 604/131, 151
See application file for complete search history.

(56) References Cited

U.S. PATENT DOCUMENTS 6,040,408 A * 3/2000 Koole ......................... 526/292.1
6,385,483 B1 * 5/2002 Uber et al. ..................... 600/431
(Continued)

FOREIGN PATENT DOCUMENTS

WO    0108730    2/2001

OTHER PUBLICATIONS

Acenbach et al. Contrast-enhanced coronary artery visualization by dual-source computed tomography-Initial experience. European journal of Radiology 57 (2006) 331-335.*
(Continued)

*Primary Examiner* — Aarti B Berdichevsky
*Assistant Examiner* — Laura Schell
(74) *Attorney, Agent, or Firm* — David Schramm; Joseph L. Kent; James R. Stevenson

(57) ABSTRACT

A method for injection of an imaging contrast into a patient, includes: a. in a first phase, injecting a fluid having a first concentration of contrast agent for a first period of time; and b. in a second phase, injecting a fluid having a second concentration of contrast agent for a second period of time. The osmolarity of the second phase is higher than the osmolarity of the first phase. The method can further include: c. in a third phase, subsequent to the second phase, injecting a fluid having a third concentration of contrast agent for a third period of time. The osmolarity of the third phase is lower than the osmolarity of the second phase. In embodiments in which the composition of the contrast agent of the third phase is the same as the composition of the contrast agent of the second phase, the third concentration can be lower than the second concentration.

38 Claims, 10 Drawing Sheets

(51) Int. Cl.
*A61M 31/00* (2006.01)
*A61K 49/04* (2006.01)

(56) References Cited

U.S. PATENT DOCUMENTS

| | | | |
|---|---|---|---|
| 6,643,537 B1 | 11/2003 | Zatezalo et al. | |
| 2004/0030288 A1* | 2/2004 | Dochon et al. | 604/131 |
| 2004/0143185 A1 | 7/2004 | Zatezalo et al. | |
| 2004/0199075 A1* | 10/2004 | Evans et al. | 600/431 |
| 2005/0053551 A1 | 3/2005 | Badiola | |
| 2006/0052690 A1* | 3/2006 | Sirohey et al. | 600/420 |
| 2006/0079768 A1* | 4/2006 | Small et al. | 600/432 |

OTHER PUBLICATIONS

Sovak M., "Contrast Media: A journey almost sentimental". Invest. Radiology 1994; 29 Supplemental 1: S4-S14.

Speck U., "Principles and Aims of Preclinical Testing.", Invest. Radiology 1994, 29 Supplemental 1: S15-S20.

Gierada D.S., Bae, K.T., "Gadolinium as a CT Contrast Agent: Assessment in a Porcine Model". Radiology 1999; 210: 829-834.

Morcos, S.K. et al, "Adverse reactions to idinated contrast media". Eur. Radiology 2001:11: 1267-1275.

Knollmann, F. et al., "Jodeinbringungsgeschwindigkiet Verschieden Konzentrierter Rontgen-Kontrastmittel bei schneller venoser Injection." Fortschr Rontgenstr 200f: 176: 88-884.

Bae, K.T. et al. "Uniform vascular contrast enhancement and reduced contrast medium volume achieved by using exponentially decelerated contrast material injection method". Radiology 2004; 231: 732-736.

Schoellnast H., et al. "Abdominal multidetector row computed tomography: reduction of cost and contrast material dose using saline flush". J. Comput. Assist. Tomography: 2003; 27: 847-853.

International Preliminary Report on Patentability for counterpart PCT application No. PCT/US2007/70497.

Bae, K.T. et al., "Peak contrast enhancement in CT and MR angiography: when does it occur and why?", Pharmacokinetic study in a porcine model, Radiology 2003; 227(3): 809-816.

Bae, K.T. et al., "Multiphasic injection method for uniform prolonged vascular enhancement at CT angiography: pharmacokinetic analysis and experimental porcine model", Radiology 2000; 216 (3): 872-880.

International Search Report and Written Opinion for counterpart PCT application No. PCT/US2007/70497.

H-J Weinmann, W-R Press, H Gries. Tolerance of extracellular contrast agents for magnetic resonance imaging. Invest Radiol 1990; 25: S49-S50.

Schwilden, A General Method for Calculating the Dosage Scheme in Linear Pharmacokinetics, European Journal of Clinical Pharmacology, 1981, pp. 379-386, vol. 20.

\* cited by examiner k1 = k2 = k3 = k4 + k5 + k6 = 6.5 l/min (ca. 110 ml/s); k5, k6 = 5 ml/s; V5, V6: 40 ml $V_{total}$ = sum $(V_i)$; $k_i$ = $k_{total}$ = constant

```
Clear g ; Clear x ; Clear h ; Clear k0 ; Clear k1 ; Clear k2 ; Clear k3 ; Clear k4 ; Clear k5 ; Clear k6 ;
Clear y1 ; Clear y2 ; Clear y3 ; Clear y4 ; Clear y5 ; Clear y6 ; Clear V1 ; Clear V2 ; Clear V3 ; Clear V4 ; Clear V5 ;
Clear V6 ; Clear Cg ; Clear Vg ; Clear H1 ;
k10= 110; k20= 110; k30= 110; k40= 100; k50= 5; k60= 5;
"input flow1"; k00 = 5;
"input flow2"; k01 = 5;
"flux end cm1"; x0 = 20;
"flux end cm2"; x1 = 30;
"cm1 concentration"; y00 = 370;
"cm2 concentration"; y01 = 115;
V1 = 250; V2 = 600; V3 = 250; V4 = 6000; V5 = 40; V6 = 40;
Vg= V1+ V2+ V3+ V4+ V5+ V6;
ras= g x_  := If x< x0, y00,  If x< x1, y01, 0   ;
kas= k0 x_  := If x< x0, k00,  If x< x1, k01, 0   ;
aas= k1 x_  := k10;
bas= k2 x_  := k20;
cas= k3 x_  := k30;
das= k4 x_  := k40;
eas= k5 x_  := k50;
fas= k6 x_  := k60;
Print "input flow rate" ; Plot k6 x + k0 x , x, 0, 100
Print "input concentration profile" ; Plot g x , x, 0, 100
result= NDSolve  y1' x § -k1 x *y1 x +k4 x *y4 x +k5 x *y5 x + k6 x +k0 x  *y6 x    V1,
    y2' x § k1 x *y1 x - k2 x *y2 x    V2,
    y3' x § k2 x *y2 x - k3 x *y3 x    V3,
    y4' x § k4 x *y3 x - k4 x *y4 x    V4,
    y5' x § k5 x *y3 x - k5 x *y5 x    V5,
    y6' x § k6 x *y3 x + k0 x *g x - k6 x +k0 x  *y6 x    V6,
    y1 0 § 0, y2 0 § 0, y3 0 § 0, y4 0 § 0, y5 0 § 0, y6 0 § 0 , y1, y2, y3, y4, y5, y6 , x, 0, 2000
Print "right heart" ; Plot y1 x  . result, x, 0, 100
Print "lung" ; Plot y2 x  . result, x, 0, 100
Print "left heart" ; Plot y3 x  . result, x, 0, 100
Print "systemic blood" ; Plot y4 x  . result, x, 0, 100
Print "aorta" ; Plot y5 x  . result, x, 0, 100
Print "input vein" ; Plot y6 x  . result, x, 0, 100 ;
Table y5 x  . result, x, 0, 100, 1 ;
Do Print y5 x  .        , x, 0, 100, 1 ;
Cg= y00* x0+ x1- x0 *y01 ;
Print Cg ;
Print V1 ; Print V2 ; Print V3 ; Print V4 ; Print V5 ; Print V6 ;
Vg= V1+ V2+ V3+ V4+ V5+ V6;
Print "total volume" ; Print Vg ;
H1=  y00* x0+ x1- x0 *y01 * k00   V1+V2+V3+V4+V5+V6 ;
Print "blood concentration" ;
Print H1 ;
```

Fig. 2C

SYSTEMS AND METHOD OF DELIVERING FLUIDS TO A PATIENT OF VARYING CONCENTRATION

CROSS REFERENCE TO RELATED APPLICATIONS

This application claims an invention which was disclosed in International Application PCT/US2007/70497 filed Jun. 6, 2007. The benefit under 35 USC §365 of the International application is hereby claimed, and the aforementioned application is hereby incorporated herein by reference. This International application claims an invention that was disclosed in U.S. Provisional Application No. 60/804,011, filed Jun. 6, 2006, the disclosure of which is incorporated herein by reference.

BACKGROUND OF THE INVENTION

The present invention relates to systems and methods of delivering fluids to a patient of varying concentration and, particularly to the delivery of contrast media used in contrast enhanced imaging procedures in varying concentrations to provide improved concentration or enhancement profiles.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

To enhance the contrast of tissue or vessels in radiodiagnostics, particularly in X-Ray Computed Tomography (CT), contrast media are used, which are characterized by the fact that they absorb or scatter X-rays more significantly than does normal tissue. For parenteral administration, there are a multiplicity of tri-iodinated aromatic compounds available, which are characterized by the fact that the introduced hydrophilic residues (side groups) lead to a high tolerance. Even at high concentrations these molecules show almost no chemotoxicity. See, for example, Sovak M. Contrast Media: A journey almost sentimental. Invest Radiol 1994; 29 Supplement1: S4-S14; Speck U. Principles and aims of preclinical testing. Invest Radiol 1994; 29 Supplement 1: S15-S20.

In addition to the use of iodine (I) as an X-ray-absorbing element, gadolinium (Gd) containing MR contrast media have been investigated with respect to X-ray CT in off label-like and/or animal studies. See Gierada D S, Bae K T Gadolinium as a CT Contrast Agent: Assessment in a Porcine Model. Radiology 1999; 210: 829-834.

A distinction is made between ionic and non-ionic contrast media, each of which can be classified further according to monomers or dimers. Generally speaking, ionic contrast media do show adverse reactions more frequently than non-ionic contrast media, which can be partly attributed to the higher osmotic pressure of ionic contrast media as compared to non-ionic contrast media. Ionic contrast media also have a net charge (electronegative) that can lead to side effects, allergic reactions etc. Non-ionic and dimeric iodine containing contrast can be manufactured to be virtually iso-osmolar (that is, having the same osmotic pressure as blood plasma) even at diagnostically relevant concentrations. However, these solutions are highly viscous. In addition the discussion regarding delayed reactions of dimeric X-ray contrast media has not yet been concluded. See for example. S K Morcos, H S Thomsen. Adverse reactions to iodinated contrast media. Eur Radiol 2001; 11: 1267-1275.

A representative list of iodine (I) containing X-ray contrast media and gadolinium (Gd) containing MRI contrast agents are set forth in Table 1. The list is not complete, but sets forth many commonly used contrast media.

TABLE 1

Representative X-ray and MRI contrast media.

| | | INN |
|---|---|---|
| Iodine containing monomers | Ionic | Acetrizoate |
| | | Amidotrizoate |
| | | Diatrizoate |
| | | Iodamide |
| | | Ioglicic Acid |
| | | Iothalamate |
| | | Ioxitalamis Acid |
| | | Metrizoate |
| | Non-Ionic | Iohexol |
| | | Iomeprol |
| | | Iopamidol |
| | | Iopentol |
| | | Iopromid |
| | | Ioversol |
| | | Ioxilan |
| | | Metrizamide |
| Iodine containing dimers | Ionic | Ioxaglate |
| | Non-Ionic | Iodixanol |
| | | Iosimenol |
| | | Iotrolan |
| Gd containing monomers | Ionic | Gadobenate |
| | | Gadopentetate |
| | | Gadoterate |
| | | Gadoversetamide |
| | | Gadoxetate |
| | Non-Ionic | Gadobutrol |
| | | Gadodiamide |
| | | Gadoteridol |
| Gd containing di- and oligomers | Ionic | — |
| | Non-Ionic | — |

A number of X-ray-physical parameters of the imaging system or scanner affect the resultant image (for example, X-ray tube: anode material, high voltage, X-ray filter, mAs-product, detector: number of slices and material). X-ray density is an important parameter for the representation of vessels. Typically, high X-ray density is desirable during the period of examination. Not only is the maximum X-ray density important, but a sufficient contrast concentration in the surrounding tissue should be achieved. Further, the concentration should be maintained locally for the X-ray density to attain a desired or optimal (value) beyond the detection period. However, simply increasing the concentration of the contrasting element does not automatically result in an optimal structuring of local and temporal X-ray contrast. In that regard, an increase of the concentration often accompanies a distinct increase in the solutions' viscosity and osmolarity/osmolality. An increased viscosity can limit the rate of administration, and an increased osmolarity/osmolality can limit the tolerability. The correlation between contrast medium concentration and viscosity has been investigated in model studies with respect to the limitation of the application velocity by high contrast media concentrations or viscosities. See F Knollmann, K Schimpf, R Felix. Jodeinbringungsgeschwindigkeit verschieden konzentrierter Röntgen-Kontrastmittel bei schneller venöser Injektion. Fortschr Röntgenstr 2004; 176: 880-884. It has been shown for Iopromide that a higher iodine flux rate of 2400 mg I/s as compared to 2220 mg I/s could be reached for a 300 mg I/ml solution with respect to the higher concentrated 370 mg I/ml solution as a result of an increase of the application flow rate from 6 to 8 ml/s, respectively. These results can be explained on the basis of the Hagen-Poiseuille law for laminar flows, where for constant pressure $\Delta P$ the volume flux rate w within vessels of radius r and length l is indirectly proportional to the viscosity $\eta$ according to $w=\pi/8\ r^4\ \Delta P/(l\eta)$.

Along with the initial concentration of the stock contrast medium solution, the type of administration plays an important role. A test bolus can be used to correlate administration time with image recording time, to prevent an unnecessary radiation-dose burden, to achieve an appropriate scan timing with respect to a contrast bolus and/or to avoid suboptimal image quality. Further, Bae et al. varied the administration rate in such a manner in attempting to optimize a bolus in the target tissue. Bae K T, Tran H Q, Heiken, J P. Uniform vascular contrast enhancement and reduced contrast medium volume achieved by using exponentially decelerated contrast material injection method. Radiology 2004; 231: 732-736. Using a stock solution with high iodine content and high viscosity, as well as a high osmolarity/osmolality, the rate of administration was selectively reduced. Another administration possibility is to administer additionally a physiologically adjusted saline solution after administering the stock solution, which contains the contrasting element. Aside from the "rinsing effect" of the delivery system and the infusion vein, the advantages of bolus formation and a reduction of contrast medium volume are also being discussed. See Schoellnast H, Tillich M, Deutschmann H A, Deutschmann M J, Fritz G A, Stessel U, Schaffler G J, Uggowitzer M M. Abdominal multidetector row computed tomography: reduction of cost and contrast material dose using saline flush. J Comput Assist Tomogr. 2003; 27: 847-53.

In both cases, profile shaping by deceleration and by use of saline flushes, one is left with the administration of the stock solutions with a high concentration of contrast medium. There is a clear indication that an increased radiographic contrast is always related to the administration of a contrast medium containing, for example, a high iodine concentration, so that strongly increased iodine concentrations will also have to be expected in the infusion vein, up to the vena cava and the right heart. The previous procedure of choice was to increase the radiographic contrast in the target area by always increasing the concentration of the stock solution or by selecting a high rate of administration for this stock solution, resulting automatically in high concentrations all the way up to the right heart along with the concomitant adverse reactions.

It remains desirable to develop improved systems and method for delivering pharmaceuticals such as contrast media to a patient.

SUMMARY OF THE INVENTION

In one aspect, the present invention provides a method for injection of an imaging contrast into a patient, including: a. in a first phase, injecting a fluid having a first concentration of contrast agent for a first period of time; and b. in a second phase, injecting a fluid having a second concentration of contrast agent for a second period of time. The osmolarity of the second phase is higher than the osmolarity of the first phase. In several embodiments in which the contrast agent of the first phase is of the same composition as the contrast agent of the second phase, the second concentration can be higher than the first concentration. The first phase can, for example, precede the second phase. The method can further include the step of c. in a third phase, subsequent to the second phase, injecting a fluid having a third concentration of contrast agent for a third period of time. The osmolarity of the third phase is lower than the osmolarity of the second phase. In embodiments in which the composition of the contrast agent of the third phase is the same as the composition of the contrast agent of the second phase, the third concentration can be lower than the second concentration. The fluid injected in the first phase can, for example, be closer to the osmolarity of blood than the fluid injected in the second phase and can even be generally iso-osmolar to blood plasma (for example, within 20% or even 10% or less of the osmolarity of blood plasma of the patient). Likewise, the fluid injected in the third phase can be closer to the osmolarity of blood plasma than the fluid injected in the second phase and can even be generally iso-osmolar to blood.

In general, most stock solutions of contrast medium have an osmolarity greater than twice (or even thrice) the osmolarity of blood plasma. In several embodiments of the present invention, the lower-concentration injection phase or phases have an osmolarity less than twice the osmolarity of blood plasma. In other embodiments, the osmolarity is less than 50% greater than that of blood plasma. In other embodiments, the osmolarity is within 20% (higher or lower) of the osmolarity of blood plasma. In still other embodiments, the osmolarity is within 10% (higher or lower) of the osmolarity of blood plasma. In even other embodiments, the osmolarity is within 5% (higher or lower) of the osmolarity of blood plasma. The osmolarity of blood plasma can be based upon an average osmolarity across numerous patients or can be measured for a particular patient.

Osmolarities, concentrations etc. in a particular phase can be an average value in the case that such a value changes during a phase.

In several embodiments, the fluid injected in the first phase includes an admixture of physiological saline and contrast agent or an admixture of a blood expander and contrast agent. The fluid injected in the first phase can have a lower viscosity than the fluid injected in the second phase. For example, the first phase can, for example, have a viscosity that is approximately equal to the viscosity of a physiological saline solution or of blood plasma. In one embodiment, the fluid injected in the first phase has a viscosity of less than $9\times10^{-3}$ Pa·s (9 centipoise). In another embodiment, the fluid injected in the first phase has a viscosity of less than $5\times10^{-3}$ Pa·s (centipoise). In a further embodiment, the fluid injected in the first phase has a viscosity of less than $3\times10^{-3}$ Pa·s (centipoise). The fluid in the first phase can, for example, be delivered in a volume of 0 to 200 ml per patient.

In several embodiments, the fluid injected in the third phase includes an admixture of physiological saline and contrast agent or an admixture of a blood expander and contrast agent. The fluid injected in the third phase can have a lower viscosity than the fluid injected in the second phase. The fluid injected in the third phase can, for example, have a viscosity that is approximately equal to the viscosity of a physiological saline solution or of blood plasma. The fluid injected in the third phase can have a viscosity of less than 9 centipoise. The fluid injected in the third phase can also have a viscosity of less than 5 centipoise. The fluid injected in the third phase can further have a viscosity of less than 3 centipoise. The fluid in the third phase can, for example, delivered in a volume of 0 to 200 ml per patient.

Likewise, the fluid in the second phase can be delivered in a volume of 0 to 200 ml per patient. The fluid in the second phase can also be delivered in a volume of up to 150 ml per patient.

In a number of embodiments, the injection rate of the first phase is equal to or greater than the injection rate of the second phase. The injection rate of the third phase can be equal to or greater than the injection rate of the second phase.

In several embodiments, the first concentration and the third concentration are approximately equal. Fluid in the first phase and the fluid in the third phase can, for example, be delivered from a first source and the fluid in the second phase can be delivered from a second source.

In a number of embodiments, a first source of a diluent fluid is provided and a second source of a second fluid having a concentration of contrast agent is provided. The fluid in the first phase can, for example, be formed by mixing the diluent fluid and the second fluid. Similarly, the fluid in the third phase can be formed by mixing the diluent fluid and the second fluid. The diluent fluid can, for example, be water, physiological saline, an aqueous solution of at least one blood expander or pharmaceutical excipients. The fluid in the second phase can, for example, can be formed by mixing the diluent fluid and the second fluid.

Contrast agent suitable for use in the present invention can, for example, include at least one of Br, Zr, Te, I, La, Ce, Pr, Nd, Sm, Eu, Gd, Tb, Dy, Ho, Er, Tm, Yb, Lu, Pt, Au, Hg, Pb and Bi. In several embodiments, the contrast agent includes at least one of an iodine containing monomer, an iodine containing dimer, a gadolinium containing monomer, a gadolinium containing dimer or a gadolinium containing oligomer. The contrast agent fluid can be ionic or nonionic.

In several embodiments of the present invention, the fluid in the second phase is hyperosmolar with respect to blood.

The contrast agent in any phase can include more than one contrast enhancing element.

The contrast agent can include at least one contrast enhancing element selected from the group of iodine-containing monomer, iodine containing dimers, gadolinium-containing monomer, gadolinium-containing-dimers and gadolinium-containing oligomers.

The contrast agent in the first phase can be of a different composition than contrast agent of the second phase and/or the contrast agent of the third phase (that is, including one or more different contrast enhancing element or one or more different mixtures of contrast enhancing elements). The contrast agent in the third phase can be of a different composition than contrast agent of the second phase and/or of a different composition than contrast agent of the first phase.

In another aspect, the present invention provides a method for injection of an agent into a patient, including: a. in a first phase, injecting a fluid having a first concentration of agent for a first period of time; and b. in a second phase, injecting a fluid having a second concentration of agent for a second period of time, the second concentration being equal to or higher than the first concentration. In several embodiments, the second concentration is higher than the first concentration.

In a further aspect, the present invention provides a method for injection of an agent into a patient, including: varying the concentration of the agent injected into the patient over the time of injection such that concentration is first increased and subsequently decreases. The concentration can be increased in a generally continuous manner. The concentration can also be decreased in a generally continuous manner. The concentration can alternatively be increased in a generally stepwise or other manner. Likewise, the concentration can be decreased in a generally stepwise or other manner.

In the methods of the present invention, injections into the patient can, for example, be intravenous or intraarterial.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 2C illustrates representative code for solving the equations derived from the models of FIGS. 2A and 2B.

DETAILED DESCRIPTION OF THE INVENTION

Figure 1A:
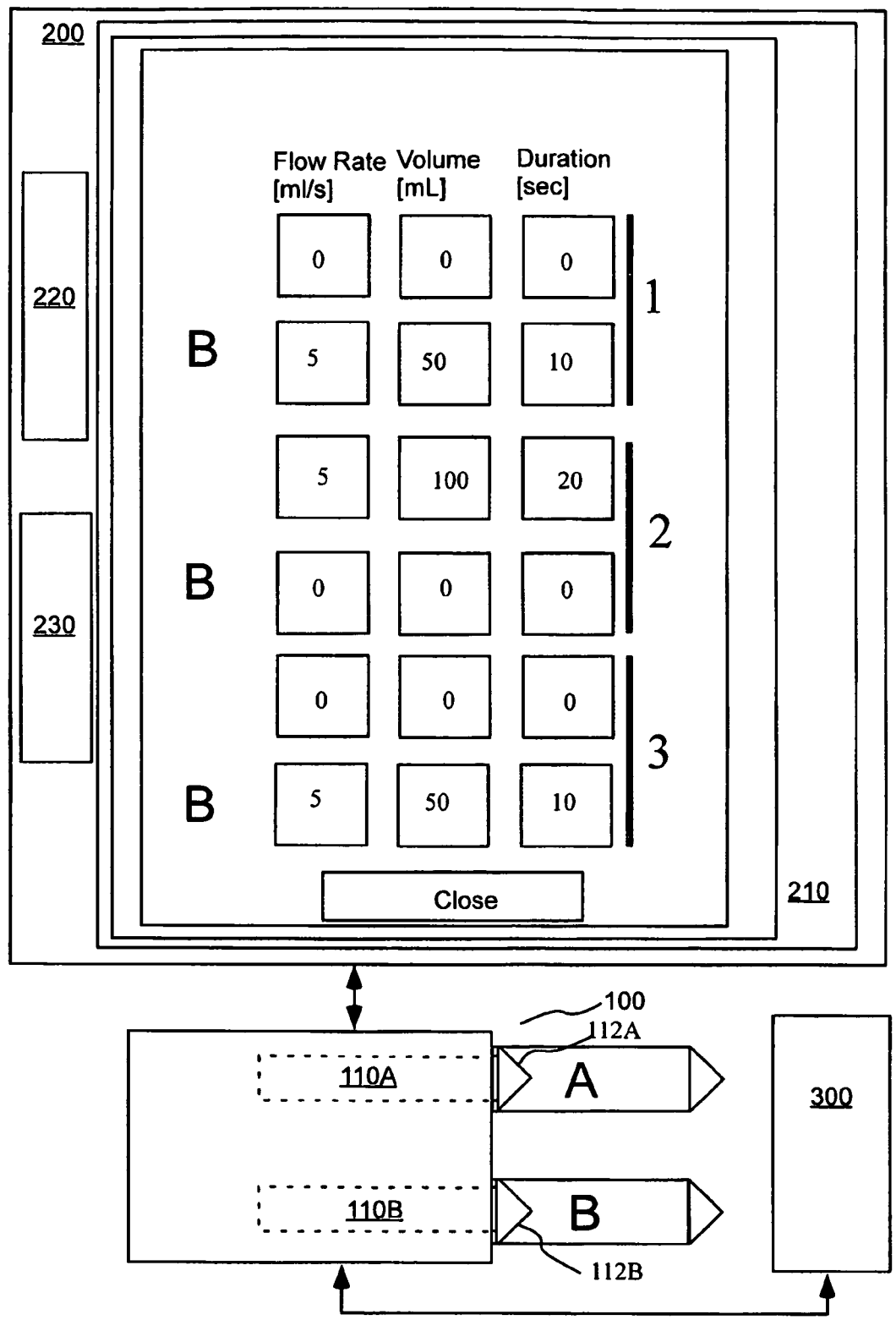
FIG. 1A illustrates and embodiment of an imaging system and injector system suitable for use in the present invention.

Use of an administration sequence combining, for example, a main or stock solution A (of higher concentration) and a secondary solution B (of a lower concentration) in studies of the present invention showed that the concentrations can be kept constant and under a critical value within the paths of administration, while increasing the concentration in the target area (as compared to prior techniques). Such administration sequences and associated advantages are described further below.

In several embodiments of the present invention, the stock solution A contains contrast medium at a relatively high concentration and contributes predominantly to the image contrast. Viscosity and osmolarity/osmolality values of solution A are higher than and normally well above those values of blood plasma. In contrast the secondary solution B can contain the contrast agent/medium at a lower concentration than stock solution A, having viscosity and/or osmolarity/osmolality closer to that of blood plasma (and lower than the corresponding values of solution A). Osmolarity is a measure of the osmoles (that is, the number of moles of a chemical compound that contribute to a solution's osmotic pressure) of solute per liter of solution, while the osmolality is a measure of the osmoles of solute per kilogram of solvent.

As described above, representative embodiments of an administration sequence of the present invention include administration of a stock or working solution A preceded by and/or followed by administration of a secondary or forming solution B. Another representative embodiment of an administration sequence of the present invention includes the administration of the stock, main or working solution A flanked (before and after) by the administration of the secondary or forming solution B. Generally, the secondary solution B, which can been adjusted to be generally iso-osmolar and to have about the same or lower viscosity as that of blood plasma, is administered first. Subsequently, the administration of the stock solution A takes place with osmolarity/osmolality and viscosity values distinctly above the plasma values, followed again by the administration of the secondary solution B. The first administration of the secondary solution is sometimes referred to herein as the preparation phase. The second administration of secondary solution is sometimes referred to herein as the form or regeneration phase. In justified cases, the preparation and/or form phase can be foregone or replaced by the administration of a physiological saline solution or other isio-osmolar solutions, (for example, exogenous plasma expanders, such as dextrans, gelatin products or hydroxyethyl starch or other biodegradable excipients). The administration sequences of the present invention can be used to optimize local agent concentrations (for example, to optimize image contrast), while diminishing or eliminating adverse side effects of hyperosmolar media (for example, contrast media). Other media, including therapeutic drugs can also benefit from the administration sequences of the present invention.

A representative embodiment of an injector system suitable for use in the present invention is illustrated in FIG. 1A. A dual syringe injector system such as system 100 illustrated in FIG. 1A is, for example, described in U.S. Pat. No. 6,643,537 and Published PCT International Patent Application No. WO 01/08730 A1. System 100 includes two fluid delivery sources (sometimes referred to herein as source "A" and source "B" herein; such as syringes or bulk containers suitable for multi-patient use) that are operable to introduce a first fluid (solution A) and/or a second fluid (for example, solution B) to the patient independently (for example, simultaneously, simultaneously in different volumetric flow proportion to each other, or sequentially or subsequent to each other (that is, A then B, or B then A)). In the embodiment of FIG. 1A, source A is in operative connection with a pressurizing mechanism such as a drive member 110A, and source B is in operative connection with a pressurizing mechanism such as a drive member 110B. The injection system includes a controller 200 in operative connection with injector system 100 that is operable to control the operation of drive members 110A and 110B, and thereby to control injection of fluid A (for example, contrast medium) from source A and injection of fluid B (for example, saline) from source B, respectively. Controller 200 can, for example, include a user interface comprising a display 210. In the illustrated embodiment, display 210 sets forth areas for parameters for injection flow rate, injection volume and injection duration for, for example, three phases of injection of fluid/solution A and/or fluid/solution B.

Controller 200 can also include a processor 220 (for example, a digital microprocessor as known in the art) in operative connection with a memory 230. Software embodying control algorithms for systems and methods of the present invention can, for example, be stored in memory 230 and executed by processor 220. As clear to one skilled in the art, all or a portion of the functionality of the methods and/or systems of the present invention can alternatively reside in an imaging system 300 and/or in a separate device and/or system.

Imaging system 300 can, for example, be a CT system, a Magnetic Resonance Imaging (MRI) system etc. The injection system can be in communicative connection with imaging system 300 and one, a plurality or all the components of the injection system and imaging system 300 can be integrated or can be incorporated in another, separate component that is placed in communicative connection with other system components.

Model calculations set forth herein demonstrate the advantages of using the flanking phases (preparation and/or regeneration phases). Representative physical parameters of solutions A and B used in studies of the present invention are summarized in Table 2.

TABLE 2

Physical parameters of the solutions A and B.

| Stock or Working Solution A | Form or Secondary Solution B |
|---|---|
| High concentration of the substance containing the contrasting element or the contrasting elements, e.g. Iopromide at 370 mg I/ml. | Concentration of the substance containing the contrasting element or the contrasting elements adjusted to be iso-omolar/iso-osmolal, (for example, Iopromide at, for example, 115 or 150 mg I/ml). |
| Osmolarity/Osmolality of the solution ≥ Osmolarity/Osmolality of blood plasma. | Osmolality/Osmolarity of the solution = or ≈ Osmolality/osmolarity of blood plasma |
| Viscosity of the solution > Viscosity of blood plasma. | Viscosity of the solution ≤ Viscosity of blood plasma. |

Figure 1B:
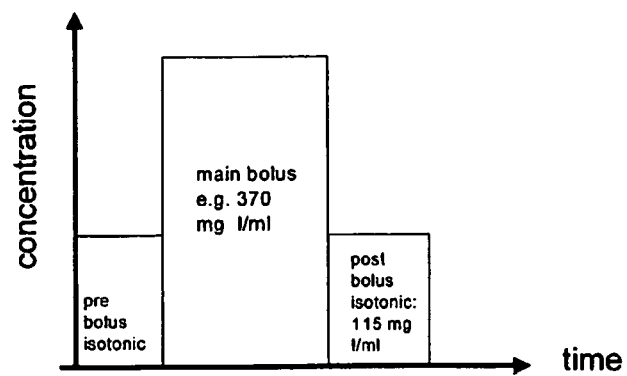
FIG. 1B illustrates an embodiment of an administration sequence of present invention, setting forth concentration of contrast enhancing agent injected versus time.

FIG. 1B illustrates a representative administration sequence including a preparation phase (pre bolus), a main phase and a regeneration phase (post bolus). During the preparation and the regeneration phase, for example almost iso-osmolar Topromide is administered in a concentration of 115 mg I/mL; for the main bolus in the example, Topromide was selected in a concentration of 370 mgI/mL.

Figure 2A:
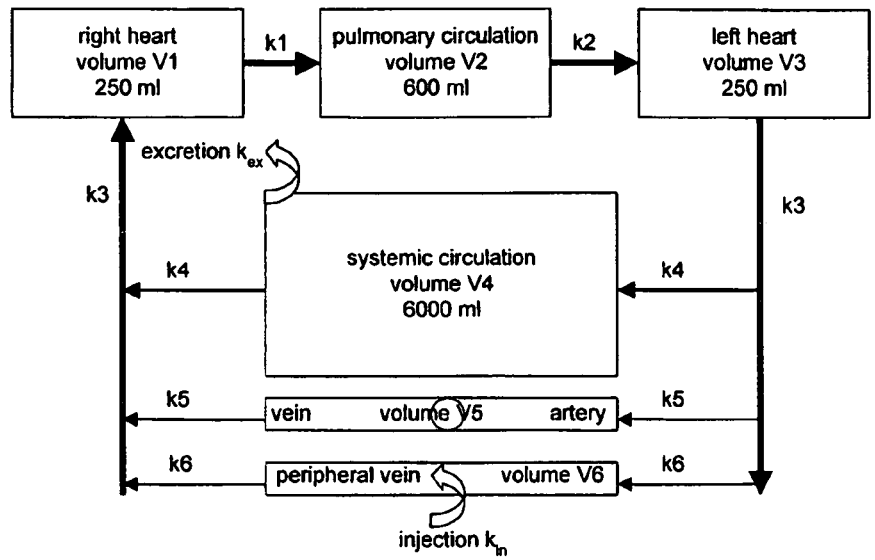
FIG. 2A illustrates a blood circulation model used in the present studies.
Figure 2B:
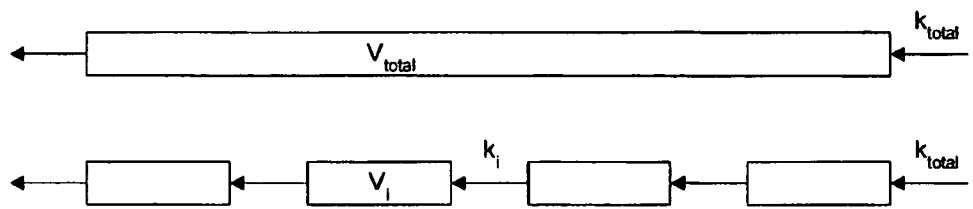
FIG. 2B illustrates a refinement of the blood circulation model of FIG. 2A for a vessel of interest.

Model calculations were based on a circulation model, which is shown in FIG. 2A. FIG. 2B illustrates a refinement of the model with respect to an observation vessel. The contrast-media solutions are administered intravenously and are introduced via the vena cava into the right heart, then via pulmonary circulation into the left heart. From the left heart, the contrast media are discharged into the peripheral circulatory system. The concentration-time profile has been calculated for all compartments, one blood vessel is regarded as the target organ (abdominal aorta). For the calculations, cardio-vascular parameters were taken from S. Silbernagl & A Despopoulos: Taschenbuch der Physiologie, Georg Thieme Verlag, Stuttgart 1991. See also, Bae K T, Peak contrast enhancement in CT and MR angiography: when does it occur and why? Pharmacokinetic study in a porcine model, Radiology. 2003; 227(3):809-16 and Bae K T, Tran H Q, Heiken J P, Multiphasic injection method for uniform prolonged vascular enhancement at CT angiography: pharmacokinetic analysis and experimental porcine model, Radiology. 2000; 216(3):872-80. The program Mathematica (available from Wolfram Research, Inc. of, for example, Champlain, Ill.) was used for to solve the rate equations. A representative example of a shortened form of program code associated with a two-step or a two-phase administration sequence as described below is set forth in FIG. 2C.

Figure 3A:
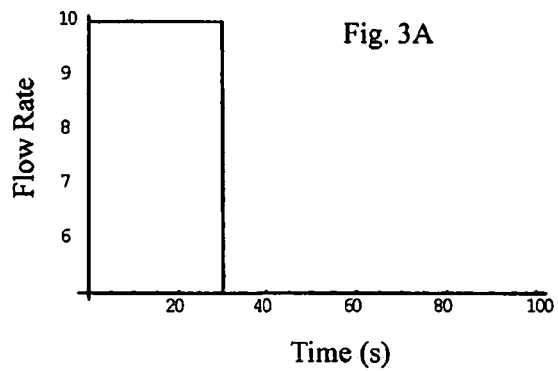
FIG. 3A sets forth the flow rate of the administration ($k_{in}+k_6$, wherein $k_6$ is constant) for a 100 ml main bolus of 400 mg I/ml followed by saline (50 ml, 10 s) at a flow rate of 5 ml/s.
Figure 3B:
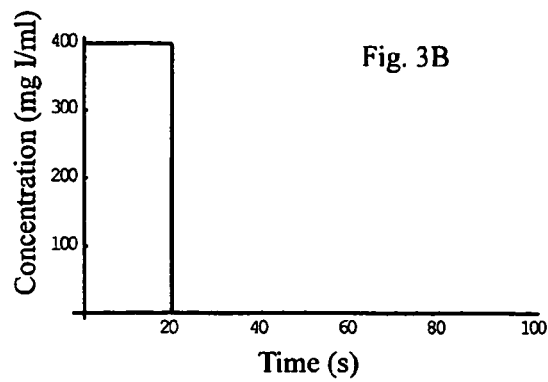
FIG. 3B sets forth the input concentration [mg I/ml] as a function of time.
Figure 3C:
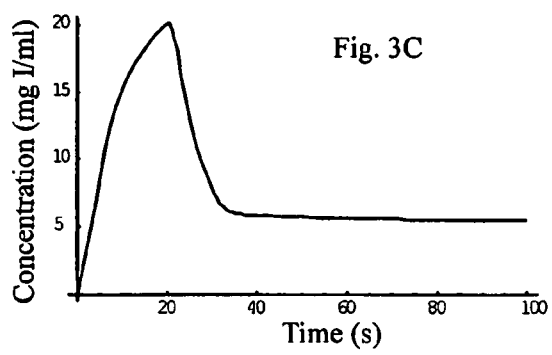
FIG. 3C sets forth the resultant modeled concentration of iodine in the right heart as a function of time.
Figure 3F:
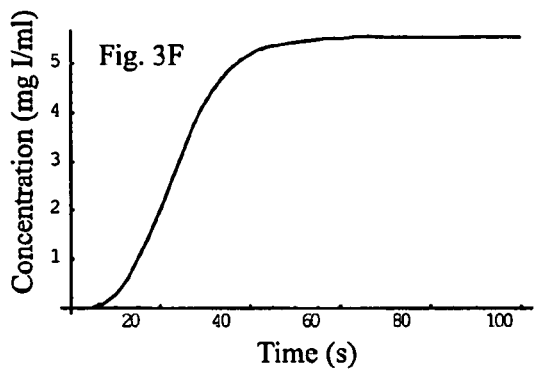
FIG. 3F sets forth the resultant modeled concentration of iodine in the systemic circulation.
Figure 3D:
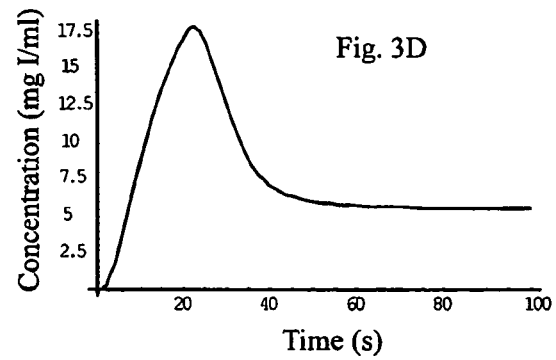
FIG. 3D sets forth the resultant modeled concentration of iodine in the lung as a function of time.
Figure 3G:
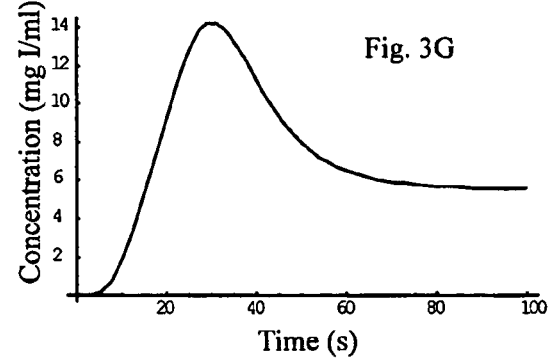
FIG. 3G sets forth the resultant modeled concentration of iodine in the aorta.
Figure 3E:
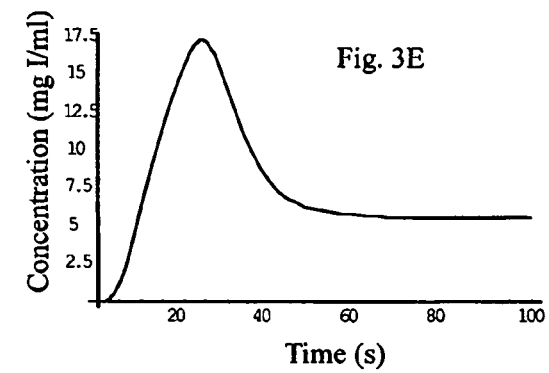
FIG. 3E sets forth the resultant modeled concentration of iodine in the left heart as a function of time.
Figure 3H:
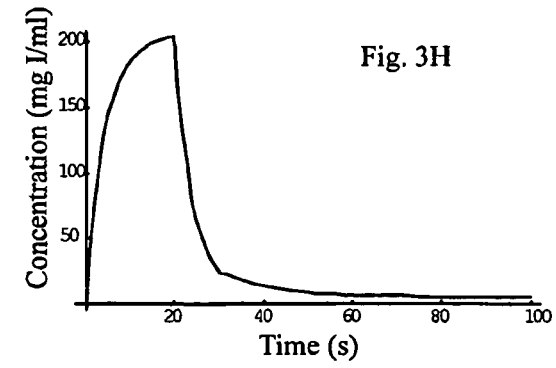
FIG. 3H sets forth the resultant modeled concentration of iodine in the input vessel.

In several representative studies, 100 ml main bolus of 400 mg I/ml followed by saline (50 ml, 10 s) at a flow rate of 5 ml/s was modeled using the model of FIG. 2A. FIG. 3A sets forth the flow rate of the administration ($k_{in}+k_6$, wherein $k_6$ is constant). FIG. 3B sets forth the input concentration [mg I/ml]. Resultant concentration profiles for a number of compartments are set forth in FIGS. 3C through 3H. In that regard, FIG. 3C sets forth the resultant modeled concentration of iodine in the right heart as a function of time. FIG. 3D sets forth the resultant modeled concentration of iodine in the lung as a function of time. FIG. 3E sets forth the resultant modeled concentration of iodine in the left heart as a function of time. FIG. 3F sets forth the resultant modeled concentration of iodine in the systemic circulation. FIG. 3G sets forth the resultant modeled concentration of iodine in the aorta (the target organ). FIG. 3H sets forth the resultant modeled concentration of iodine in the input or injection vessel.

Figure 4A:
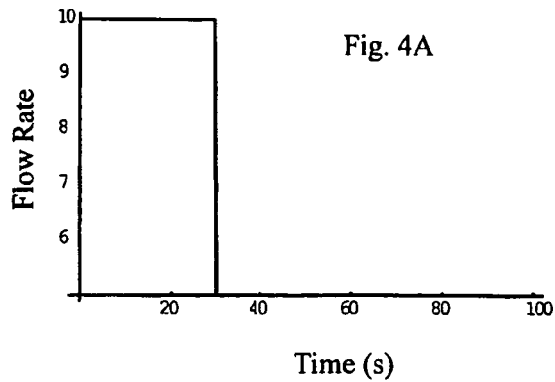
FIG. 4A sets forth the flow rate of the administration ($k_{in}+k_6$, wherein $k_6$ is constant) for an administration including injection of 370 mg I/ml (solution A; 100 ml, 20 s) followed by a 50 ml of iso-osmolar solution B of 115 mg I/ml for 10 s at a constant flow rate of 5 ml/s.
Figure 4B:
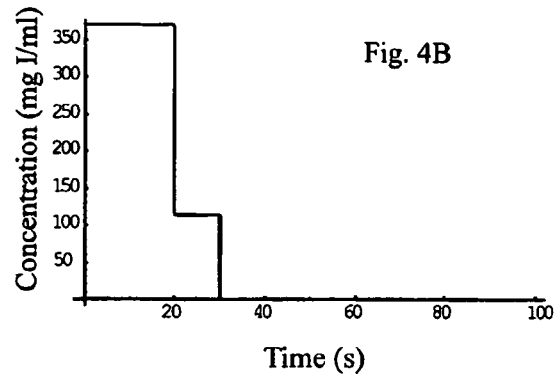
FIG. 4B sets forth the input concentration [mg I/ml] as a function of time.
Figure 4C:
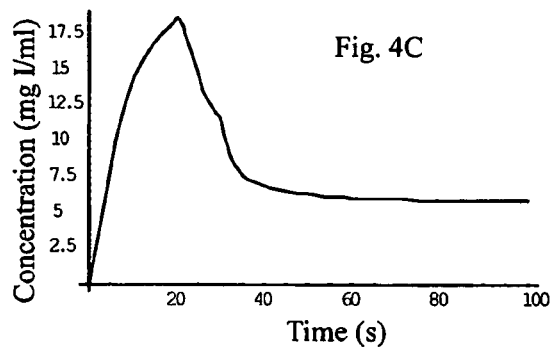
FIG. 4C sets forth the resultant modeled concentration of iodine in the right heart as a function of time.
Figure 4F:
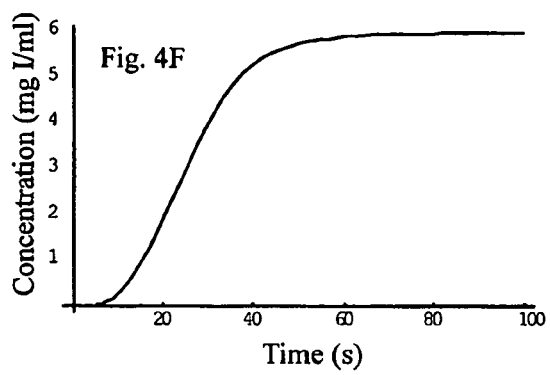
FIG. 4F sets forth the resultant modeled concentration of iodine in the systemic circulation.
Figure 4D:
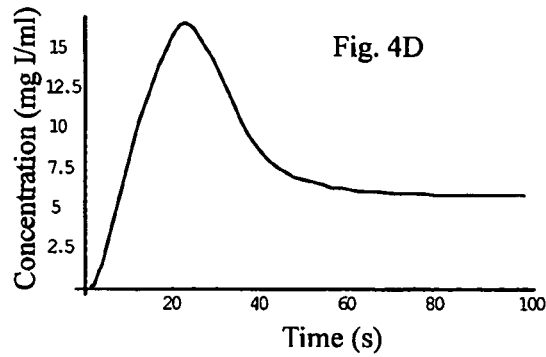
FIG. 4D sets forth the resultant modeled concentration of iodine in the lung as a function of time.
Figure 4G:
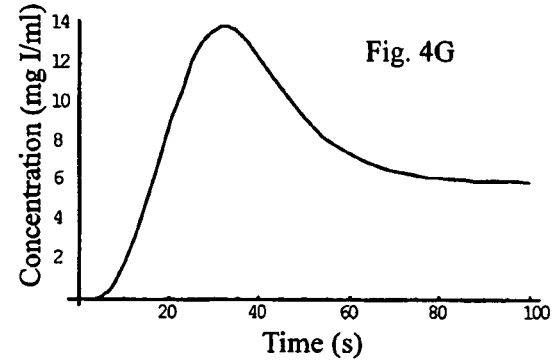
FIG. 4G sets forth the resultant modeled concentration of iodine in the aorta.
Figure 4E:
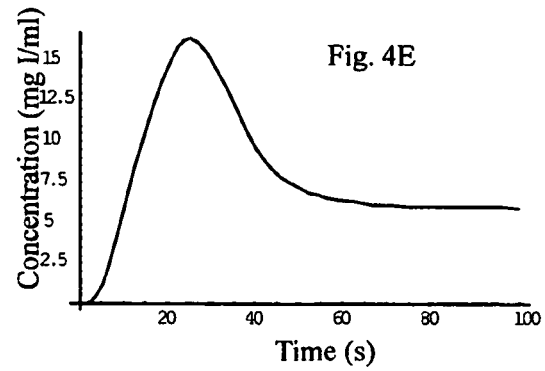
FIG. 4E sets forth the resultant modeled concentration of iodine in the left heart as a function of time.
Figure 4H:
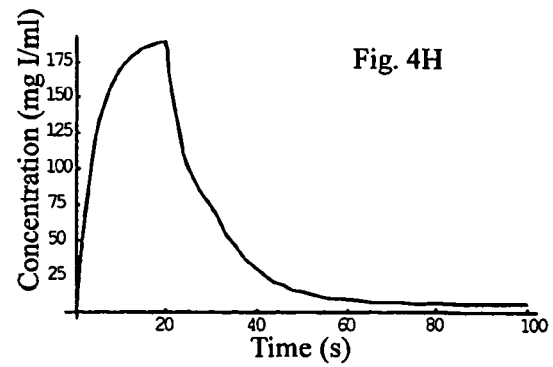
FIG. 4H sets forth the resultant modeled concentration of iodine in the input vessel.

In the representative studies of FIG. 4A through 4H, the administration included 370 mg I/ml (solution A; 100 ml, 20 s) followed by a 50 ml of iso-osmolar solution B of 115 mg I/ml for 10 s at a constant flow rate of 5 ml/s. Iso-osmolarity or iso-osmolality was assumed around 115 mg I/ml. FIG. 4A sets forth the flow rate of the administration ($k_{in}+k_6$, wherein $k_6$ is constant). FIG. 4B sets forth the input concentration [mg I/ml]. Resultant concentration profiles for a number of compartments are set forth in FIGS. 4C through 4H. In that regard, FIG. 4C sets forth the resultant modeled concentration of iodine in the right heart as a function of time. FIG. 4D sets forth the resultant modeled concentration of iodine in the lung as a function of time. FIG. 4E sets forth the resultant modeled concentration of iodine in the left heart as a function of time. FIG. 4F sets forth the resultant modeled concentration of iodine in the systemic circulation. FIG. 4G sets forth the resultant modeled concentration of iodine in the aorta. FIG. 4H sets forth the resultant modeled concentration of iodine in the input vessel.

Figure 5A:
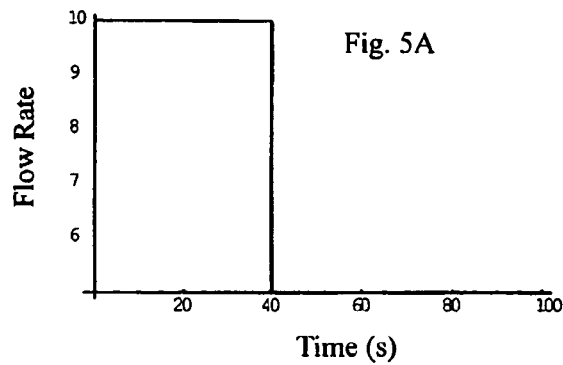
FIG. 5A sets forth the flow rate of the administration ($k_{in}+k_6$, wherein $k_6$ is constant) for an administration including injection of 50 ml of 115 mg I/ml (iso-osmolar solution B, 10 s), followed by 370 mg I/ml (solution A; 100 ml, 20 s) followed by a 50 ml of 115 mg I/ml (iso-osmolar solution B, 10 s) at a constant flow rate of 5 ml/s.
Figure 5B:
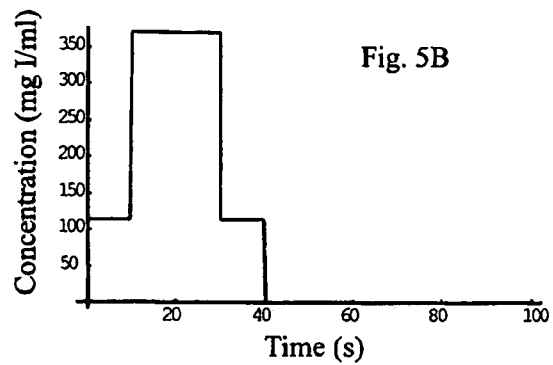
FIG. 5B sets forth the input concentration [mg I/ml] as a function of time.
Figure 5C:
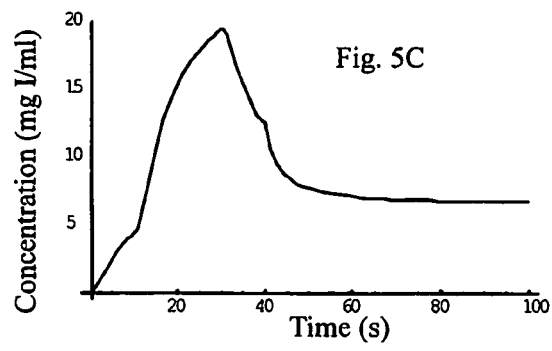
FIG. 5C sets forth the resultant modeled concentration of iodine in the right heart as a function of time.
Figure 5F:
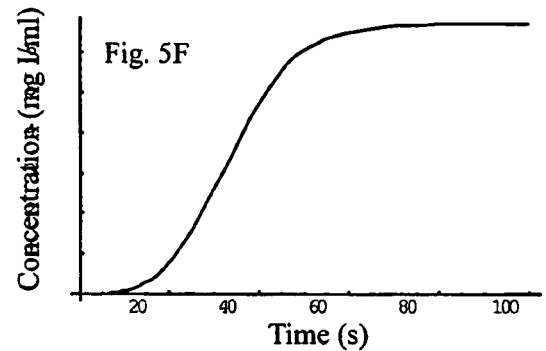
FIG. 5F sets forth the resultant modeled concentration of iodine in the systemic circulation.
Figure 5D:
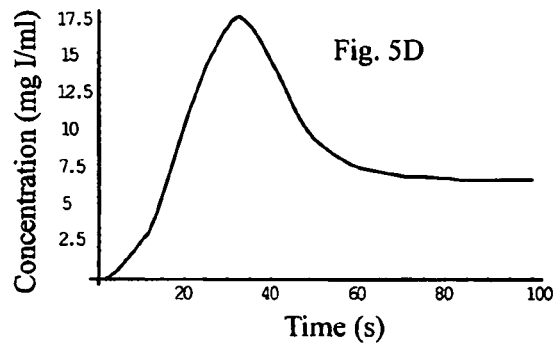
FIG. 5D sets forth the resultant modeled concentration of iodine in the lung as a function of time.
Figure 5G:
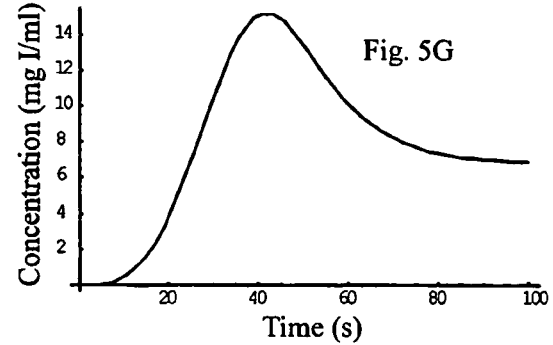
FIG. 5G sets forth the resultant modeled concentration of iodine in the aorta.
Figure 5E:
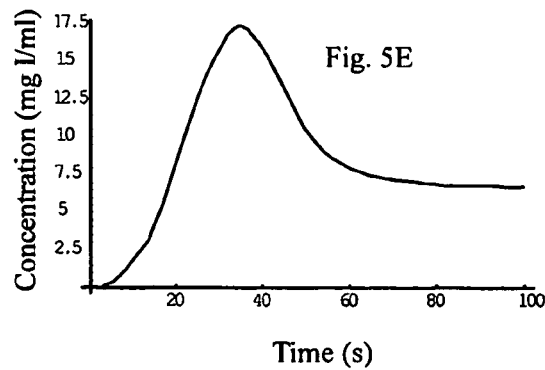
FIG. 5E sets forth the resultant modeled concentration of iodine in the left heart as a function of time.
Figure 5H:
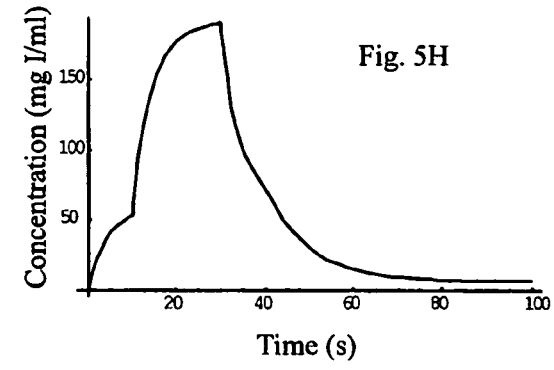
FIG. 5H sets forth the resultant modeled concentration of iodine in the input vessel.

In the representative studies of FIG. 5A through 5H, the administration included injection of 50 ml of 115 mg I/ml (iso-osmolar solution B, 10 s), followed by 370 mg I/ml (solution A; 100 ml, 20 s) followed by a 50 ml of 115 mg I/ml (iso-osmolar solution B, 10 s) at a constant flow rate of 5 ml/s. The injection parameters for the administration sequence are, for example, illustrated on display 210 of FIG. 1A. FIG. 5A sets forth the flow rate of the administration ($k_{in}+k_6$, wherein $k_6$ is constant). FIG. 5B sets forth the input concentration [mg I/ml]. Resultant concentration profiles for a number of compartments are set forth in FIGS. 5C through 5H. In that regard, FIG. 5C sets forth the resultant modeled concentration of iodine in the right heart as a function of time. FIG. 5D sets forth the resultant modeled concentration of iodine in the lung as a function of time. FIG. 5E sets forth the resultant modeled concentration of iodine in the left heart as a function of time. FIG. 5F sets forth the resultant modeled concentration of iodine in the systemic circulation. FIG. 5G sets forth the resultant modeled concentration of iodine in the aorta. FIG. 5H sets forth the resultant modeled concentration of iodine in the input vessel. In the studies of FIG. 3A through 5H, the actual concentration [mg I/mL] vs. time [s] is shown starting with the beginning of the sequence of administration.

In the studies of FIGS. 3A through 5H, the calculations were focused upon a time period of 50-100 s post injection. Effects related to extravasation and renal excretion of the contrast medium were ignored during the short observation period. In all cases, the concentrations are given in mg I/mL, which has become customary in X-ray imaging. However, any other concentrations units can also be chosen. Thus, one might prefer for the case of Gd-containing MR contrast media the concentration unit mol Gd/L. The same is true for substances with other contrast enhancing agents or elements for example (Br, Zr, the lanthanides from La to Lu, Bi etc.).

The amount of Iodine delivered to the patient under the administration sequences set forth above and for a sequence in which a single bolus of 100 ml of 370 mg I/ml (UL-TRAVIST 370) is delivered to the patient are set forth in Table 3. As set forth in Table 3, under the administration protocols set forth above, the two-step or two-phase sequence results in an increase in the amount of iodine administered (relative to the 370/0 sequence) of 16%, while the three-step-model results in an increase of 31%.

TABLE 3

Amount of Iodine Per Patient

| combination | 400/0 | 370/0 | 370/115 | 115/370/115 |
|---|---|---|---|---|
| mg I total | 40,000 | 37,000 | 42,750 | 48,500 |
| rel. to 370 [%] | 108 | 100 | 116 | 131 |

Figure 6:
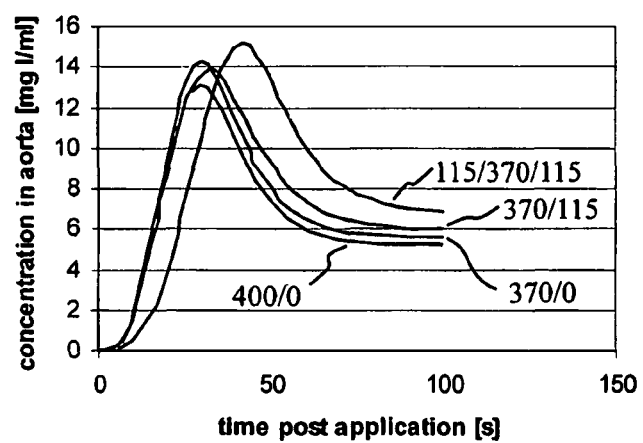
FIG. 6 illustrates a time-concentration profile within the abdominal aorta (the target organ or region of interest) after several different administration sequences.

FIG. 6 sets forth a comparison of a single administration of Topromide at 370 mg I/mL and at 400 mg I/mL with the administration of Topromide at 370 mg I/mL followed by iso-osmolar Topromide at 115 mg I/mL and with the administration of Topromide at 370 mg I/mL flanked (before and after) by 115 mg I/mL of Iopromide. There is an indication that the administration sequence with a preparation and a regeneration phase results in a maximum Topromide concentration in the abdominal aorta, though the concentration in the vena cava or right heart are below the concentration reached by the single-shot or single phase application of 400 mg I/mL. Also the period of the increased iodine concentration in the target is prolonged optimally for a three-phase sequence. Table 4 sets forth time windows for each of the above administration sequences wherein concentration is greater than a representative target or desired concentration of 10 mg I/ml in the aorta.

TABLE 4

|  | 0/400 | 370/0 | 370/115 | 115/370/115 |
|---|---|---|---|---|
| $t_{min}$ [s] | 21 | 22 | 22 | 30 |
| $t_{max}$ [s] | 43 | 41 | 47 | 60 |
| Δt [s] | 22 | 19 | 25 | 30 |

Figure 1C:
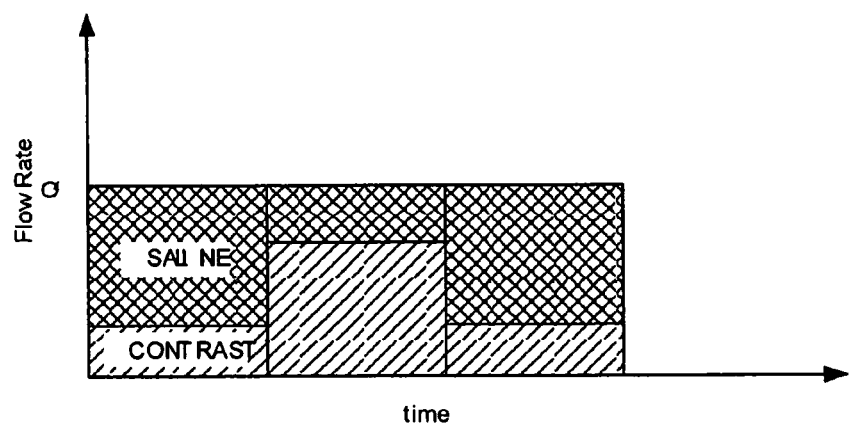
FIG. 1C illustrates an administration sequence of a first dilute solution, followed by a concentrated solution and then a second dilute solution wherein flow rate is maintained relatively constant.

In forming an administration sequence of the present invention, an initial step can be carried out in which blood is analyzed to determine osmolarity, plasma viscosity and/or other properties). For example, the hematocrit (ratio of the volume of packed red blood cells to the volume of whole blood) can be measured, which provides an estimate of blood viscosity. Additionally or alternatively, creatinine levels can be measured, which provides an indication of renal function and thereby an indication of the tolerance of a particular patient to contrast. This information can be provided to the injector control system via, for example, the hospital information system network of via communication with a bedside analysis system. The subsequent administration sequence with a stock solution A in one syringe and a lower concentration (for example, generally iso-osmolar) secondary solution B in the second syringe permits a number of other favorable uses aside from the pattern outlined in, for example, FIGS. 1B and 1C where critical concentrations in the vessels can be taken into account and are not exceeded but still maximal concentrations in the targets are reached.

Figure 7A:
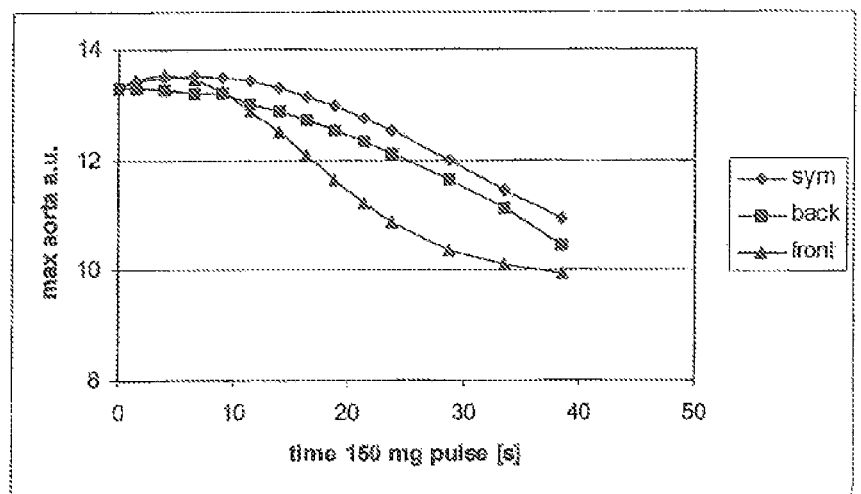
FIG. 7A illustrates a graph of peak concentration in the aorta as function of a total secondary phase (at 150 mg I/ml) period length.
Figure 7B:
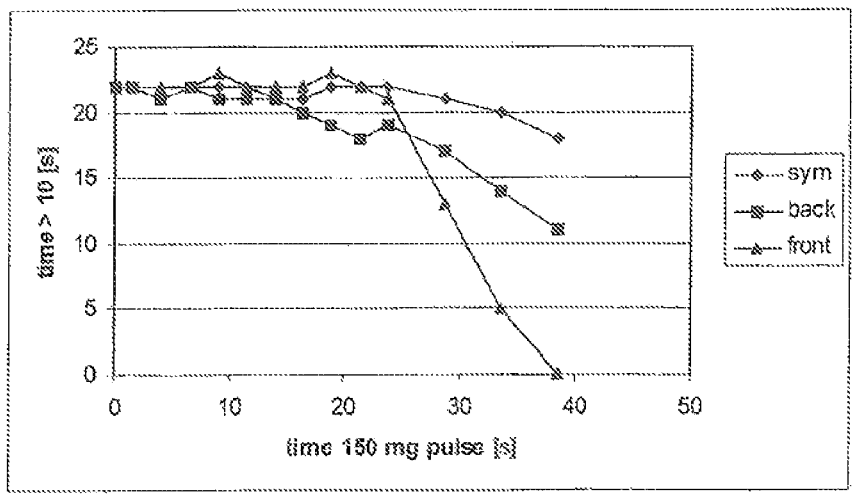
FIG. 7B illustrates a time period wherein a concentration >10 mg I/ml was maintained in the aorta as function of length of the pre/post phase period length.

Further studies using a constant flow rate of 5 ml/s are set forth in FIGS. 7A and 7B. In the studies of FIGS. 7A and 7B, the total amount of iodine administered was 40,000 mg per patient, which corresponds to the amount that would be delivered in a single phase or step of 100 ml of fluid medium having a concentration of 400 mg I/ml. In the studies of FIGS. 7A and 7B, a main bolus or phase at 370 mg I/ml was studied with a prior phase and/or a subsequent phase of 150 mg I/ml. In the studies, a concentration of 150 mg I/ml was used as that concentration is a clinically available ULTRAVIST solution (available from Schering, AG of the Republic of Germany). Three possibilities were studied: a. symmetric (sym) administration sequence (including an initial phase/bolus of 150 mg I/ml solution, followed by a main phase/main bolus of 370 mg I/ml solution, followed by another phase/bolus of 150 mg I/ml solution, wherein the pre-main and post-main phases/boluses were of equal length); b. a "back" administration sequence wherein the pre-main bolus was excluded (wherein the first phase is the main phase/bolus), but the post-main bolus of 150 mg I/ml solution was included; and c. a "front" administration sequence, wherein the pre-main phase/bolus was excluded, but the pre-main bolus/phase and the main phase were included. The length of the main phase was varied from 6 to 21.6 s which resulted in the total length of pre and post phases of 38.5 to 0 s, respectively. The results of the calculations are plotted in FIG. 7A as the maximum or peak concentration in the aorta as a function of the length of the 150 mg I/ml pre/post phase periods; and in FIG. 7B as the time period wherein a representative target concentration >10 mg I/ml was maintained in the aorta as function of length of the pre/post phase periods.

From FIGS. 7A and 7B, it can be seen that there is a shallow maximum of the concentration in the aorta under the conditions chosen at short periods of the pre/post (front/back) phase while the period wherein concentration is >10 mg I/ml in the aorta stays relatively constant over a wide range of pre/post phase lengths. The phase lengths studied are set forth in Table 5 below.

TABLE 5

| 370 mg I/ml main phase | 150 mg I/ml Pre-main or front phase | 150 mg I/ml Post-main or back phase |
|---|---|---|
| s | s | s |
| 2.00 | 48.40 | 24.20 |
| 4.00 | 43.47 | 21.73 |
| 6.00 | 38.53 | 19.27 |
| 8.00 | 33.60 | 16.80 |
| 10.00 | 28.67 | 14.33 |
| 12.00 | 23.73 | 11.87 |
| 14.00 | 18.80 | 9.40 |
| 16.00 | 13.87 | 6.93 |
| 18.00 | 8.93 | 4.47 |
| 20.00 | 4.00 | 2.00 |
| 21.00 | 1.53 | 0.77 |
| 21.62 | 0.00 | 0.00 |

With respect to the symmetric (three-step or three-phase) case, it is seen from FIG. 7A that a period of approximately 10 s for the flanking phases (or 2×5 s for the pre- and post-main phases) provides maximum concentrations. Under such conditions, the administration period or phase duration for the main phase would be close to 18 s, providing a total phase duration profile for the three phases of 5 s/18 s/5 s.

Figure 8:
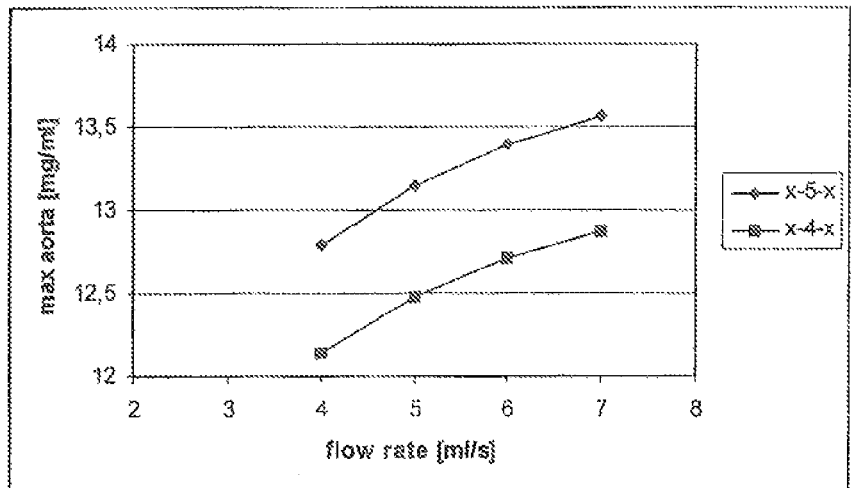
FIG. 8 illustrates maximum concentration of contrast agent in the aorta as a function of flow rate of the pre and post phases for main phases of two different flow rates in a symmetrical administration sequence.

The flow rate of any phase of the administration sequence can be varied. Indeed, as the viscosity of lower concentration solutions such as the 150 mg I/ml solution is considerably lower than the viscosity of, for example, a 370 mg I/ml solution, increased flow rates are possible. Moreover, the likelihood of substantially adverse effects on blood components is reduced with iso-osmolar or nearly iso-osmolar solutions. In FIG. 8, studies of varying flow rate are set forth for a symmetric three-phase case wherein the total amount of iodine delivered to the patient is maintained constant at 40.000 mg I. In one set of studies (x-4-x), the flow rate of the main phase was set to 4 ml/s and in another set of studied (x-5-x), the flow rate of the main phase was set to 5 ml/s, while the flow rate of administration of the secondary phase/bolus was varied. Time period (phase duration) and flow rate were adjusted so that the total amount delivered was, once again, 40.000 mg I per patient. As illustrated in FIG. 8, in both sets of studies, the maximum or peak concentration increases with increasing flow rate of the pre/post phases. The time period with concentrations >10 mg I/ml in the aorta increased slightly for the x-5-x administration sequences, while it decreased for the x-4-x administration sequence.

Figure 9A:
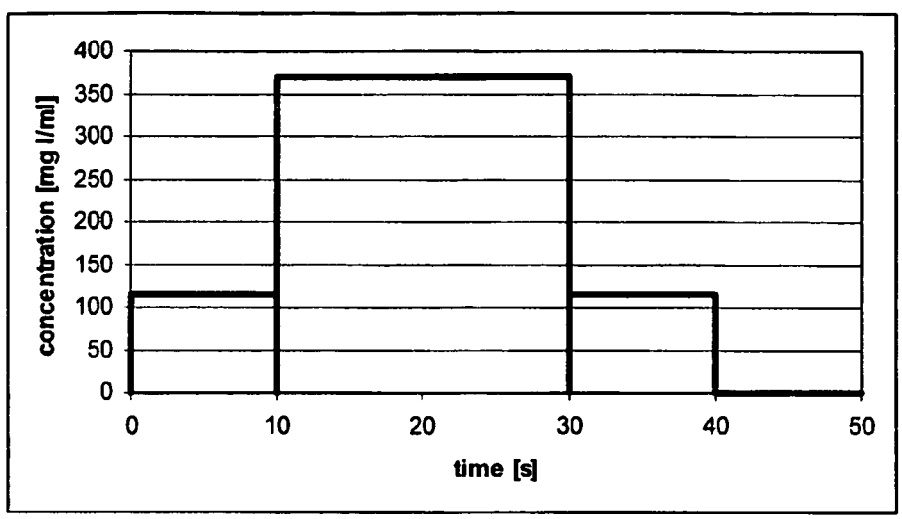
FIG. 9A illustrates an administration sequences in which injection of a higher concentration fluid is flanked (pre and post) with injections of a lower concentration (for example, iso-osmolar) fluid.

The continuous refinement of any administration profile adapted to the patient, in which any concentration profile, from generally iso-osmolar solution B to the "pure" stock (hypertonic) solution A, can be achieved by varying the feed rates of, for example, syringes or containers A and B of FIG. 1A. Accordingly, the administration sequence can be started as iso-osmolar, in which only plunger 112B of syringe B (containing the secondary solution B) is advanced. The flow rate of the secondary solution B can be reduced, while simultaneously starting the administration of the main solution A (via advancement of plunger 112A) results in maximum concentration. Subsequently, the flow rate of stock solution A can again be reduced and the secondary solution B started up to the point when, for example, once again pure secondary solution B is being administered. These profiles can be attained with a constant sum and with a variable rate of administration. It appears to be advantageous, for example, from a physiological point of view, to administer the secondary solution B for a sufficient length of time during the preparation and regeneration phase to allow the secondary solution to flow into the vena cava or right heart. Two sequences of administration discussed above are illustrated in FIGS. 9A and 9B.

In the simplest case (illustrated in FIG. 9A) of the three-step or three-phase administration sequence BAB, the advancement of the pistons 110A and 110B (and consequently, plungers 112A and 112B) in the syringes A and B is equal. While one piston is advanced, the other piston is at rest.

Figure 9B:
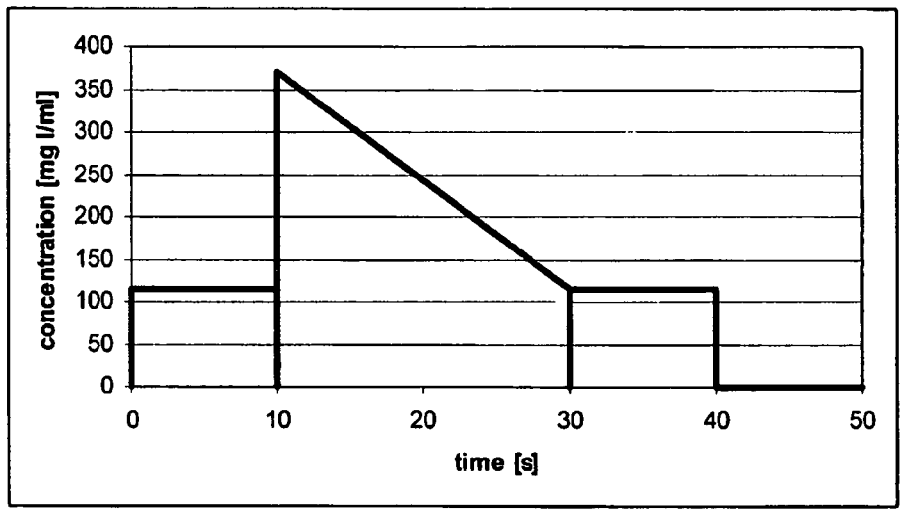
FIG. 9B illustrates an administration sequence in which a higher concentration solution B is administered with constant flow rate and, subsequently, a lower concentration solution A is administered starting with maximum flow rate, but during this phase duration or period, the flow rate of A is linearly reduced to zero, while the flow rate of B is regulated from zero to maximal velocity and kept constant for a further 10 seconds.

In the administration sequence of FIG. 9B, solution B is administered with constant flow rate. Subsequently, solution A is administered starting with maximum flow rate, but during this phase duration or period, the flow rate of A is linearly reduced to zero, while the flow rate of B is regulated from zero to a maximum flow rate and kept constant for a further 10 s. In both cases, solution A contains the working contrast medium while solution B contains the contrast medium generally iso-osmolar to blood, as described above.

In principle, the same time-profiles can be reached if solution A contains the working solution and solution B contains, for example, only water (or other diluent and no contrast enhancing agent) for injection. In that case both pistons must be advanced at different velocity to reach blood iso-osmolarity (iso-osmolality) by mixing prior to entry into the blood stream or by mixing in the blood stream. In that case the solution B is considered to be only virtually adjusted to blood iso-osmorality (iso-osmolality/isotonicity).

Figure 9C:
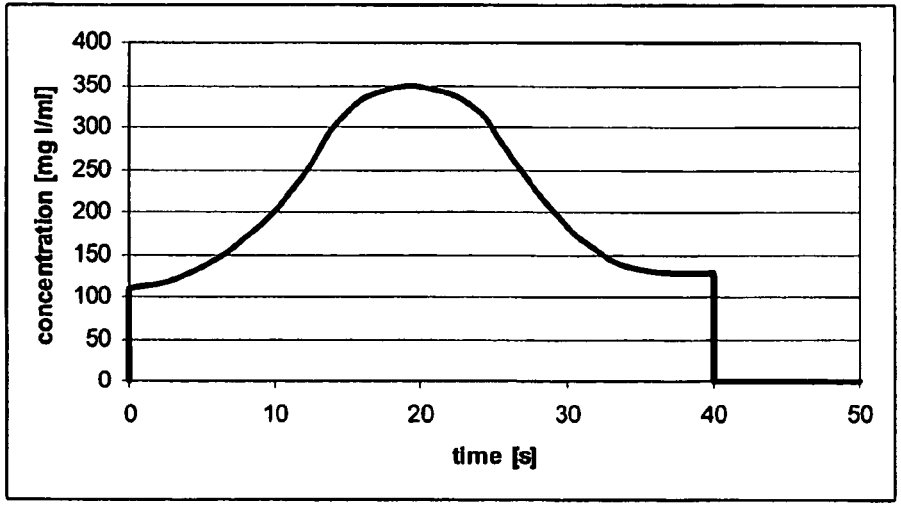
FIG. 9C illustrates an administration sequence with a continuously varying concentration.

In the administration sequence of FIG. 9C, the input is varied in a continuous manner over the time of the injection procedure. An initial, preparation phase and a subsequent regeneration phase can be defined wherein the average contrast agent concentration, viscosity and osmolarity/osmolality is less than solution A.

Advantages of the systems and methods of the present invention as compared to current procedures include, but are not limited to, that the bolus profile in the target area can be adjusted with solutions of contrast media being generally iso-osmolar (for example, within 20% or less) to blood plasma. It is known that iso-osmolar solutions lead to a minimization of possible side-effects. See, for example, H-J Weinmann, W-R Press, H Gries. Tolerance of extracellular contrast agents for magnetic resonance imaging. Invest Radiol 1990; 25: S49-S50. One can also adjust the concentration for enhancement values based on, for example, X-ray tube voltage.

In the studies discussed above, the administration of contrast enhancing fluid including iodine was discussed in several representative examples. However, various contrast agents (for example, those listed in Table 1 and/or those with different contrasting elements, such as iodine (I) and/or gadolinium (Gd)) can be administered.

For example, a number of combinations are possible with respect to the filling of the two syringes, e.g. iodine-containing contrast media for solutions A and B, iodine containing contrast media in solution A and gadolinium containing contrast media in solution B, gadolinium containing contrast medium in solution A and iodine containing contrast medium in solution B, gadolinium containing contrast media in both solutions. These four combinations refer, for example, to the administration of registered iodine containing contrast media for X-ray imaging and registered gadolinium containing MR contrast media. The administration of Gd-containing MR contrast media is discussed with respect to avoidance of iodine allergies and for patients with renal insufficiency. Moreover, administration of Gd can have X-ray physical advantages. In the case of patients with renal insufficiencies, it is also possible to use lower concentrations of contrast media, but with increased flow rate to achieve sufficient enhancement. The solutions A and B can also contain substances with other contrasting elements including, but not limited to, Br, Zr, La, Ce, Pr, Nd, Sm, Eu, Gd, Tb, Dy, Ho, Er, Tm, Yb, Lu, Pt, Au, Hg, Pb and Bi.

If different contrast media are filled into, for example, syringes A and B of FIG. 1A, mixtures are obtained if both syringes are simultaneously advanced without the need to prepare the mixtures separately (as described in Published US Patent Application No. 2005/0053551 A1). On that physiological, medical and physical basis, a rich repertoire of application sequences is available so that the administration can be individualized for the patient and for the diagnostic procedure.

In one case, solution B contains nothing but injection water (such as aqua destillatum) or saline and only by the predetermined and controlled advancement of both syringes is a generally iso-osmolar contrast media solution obtained by mixing and directly administered into a patient vessel. In this case syringe B contains a solution which is only virtually iso-osmolar to blood plasma. Further, a solid form of contrast can be held in one container (for example, a syringe) and sterile water can be held in another container. The separate elements can be mixed in appropriate ratios.

In the studies discussed above, influence on concentration profile/enhancement profile of the contrast medium bolus profile were considered. In general, it is desirable to maximize the peak concentration (or ΔHounsfield Units-HU) in the target vessel/region of interest. Moreover, a concentration or enhancement above a target concentration or enhancement should be of a reasonable duration with respect to the CT study time.

The above studies have demonstrated that a post-main flush with an iso-osmolar solution of contrast medium leads to a clear benefit over a saline flush or over an increase of the main phase concentration. This is an important advantage, since, for example, critical concentrations in the vena cava or at the entrance into the right heart can be kept under a threshold value, which is not possible via an increase of the main phase concentration, (for example, from 370 to 400 mg I/ml). In several studies, a three-step or three-phase model (wherein a main phase of relatively high concentration is flanked by two lower concentration phases that can, for example, be generally iso-osmolar to blood) was found to be superior to a two-step or two-phase model. Even under conditions where the total contrast media concentration is kept constant, contrast media administration in the form of a main bolus flanked by two secondary boli seems physically to be advantageous over only a main bolus. A reduction of the contact time of blood cells with the contrast medium at high concentration by a pre bolus flush with either saline or an iso-osmolar contrast media solution could compensate osmolarity induced side-effects and could account for critical losses of blood viscosities. The shaping of the contrast media administration by two or three phases offers advantages over the complex bolus applications since, in the present case, shaping is performed by iso-osmolar contrast media solutions. For applicators with two or more fluid sources (for example, syringes A and B) one container can, for example, be filled with the main contrast medium stock solution (having a higher concentration), while the second container can, for example, be filled with a contrast medium solution adjusted to a lower concentration (for example, to be generally iso-osmolar with blood) or filled with a diluent. Lower concentration solutions at low viscosities can be administered at higher velocities compared to more viscous solutions, which can lead to a sharpening of the concentration/enhancement profile.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A method for injection of an imaging contrast into a patient, comprising:
   a. in a first phase, injecting a fluid having a first concentration of contrast agent for a first period of time, wherein the fluid injected in the first phase is generally iso-osmolar to blood plasma;
   b. in a second phase, subsequent to the first phase, injecting a fluid having a second concentration of contrast agent for a second period of time, the second concentration being such that the osmolarity of the second phase is higher than the osmolarity of the first phase; and
   c. in a third phase, subsequent to the second phase, injecting a fluid having a third concentration of contrast agent for a third period of time, the third concentration being such that the osmolarity of the third phase is lower than the osmolarity of the second phase,
   wherein the first concentration of contrast agent includes contrast,
   wherein the third concentration of contrast agent includes contrast, and
   wherein each of the first phase, the second phase, and the third phase proceed according to a set of injection parameters, including at least one of injection flow rate, injection volume, and injection duration, determined in advance of the first phase.

2. The method of claim 1 wherein the fluid injected in the first phase comprises an admixture of physiological saline and contrast agent or an admixture of a blood expander and contrast agent.

3. The method of claim 1 wherein the fluid injected in the first phase has a lower viscosity than the fluid injected in the second phase.

4. The method of claim 1 wherein the fluid injected in the first phase has a viscosity that is approximately equal to the viscosity of a physiological saline solution or of blood plasma.

5. The method of claim 1 wherein the fluid injected in the first phase has a viscosity of less than $9 \times 10^{-3}$ Pa·s (9 centipoise).

6. The method of claim 1 wherein the fluid injected in the first phase has a viscosity of less than $5 \times 10^{-3}$ Pa·s (5 centipoise).

7. The method of claim 1 wherein the fluid injected in the first phase has a viscosity of less than $3 \times 10^{-3}$ Pa·s (3 centipoise).

8. The method of claim 1 wherein the fluid in the first phase is delivered in a volume of 0 to 200 ml per patient.

9. The method of claim 1 wherein the fluid injected in the third phase is generally iso-osmolar to blood plasma.

10. The method of claim 9 wherein the fluid injected in the third phase comprises an admixture of physiological saline and contrast agent or an admixture of a blood expander and contrast agent.

11. The method of claim 9 wherein the fluid injected in the third phase has a lower viscosity than the fluid injected in the second phase.

12. The method of claim 9 wherein the fluid injected in the third phase has a viscosity that is approximately equal to the viscosity of a physiological saline solution or of blood plasma.

13. The method of claim 9 wherein the fluid injected in the third phase has a viscosity of less than 9 centipoise.

14. The method of claim 9 wherein the fluid injected in the third phase has a viscosity of less than 5 centipoise.

15. The method of claim 9 wherein the fluid injected in the third phase has a viscosity of less than 3 centipoise.

16. The method of claim 1 wherein the fluid in the first phase is delivered in a volume of 0 to 200 ml per patient.

17. The method of claim 1 wherein the fluid in the third phase is delivered in a volume of 0 to 200 ml per patient.

18. The method of claim 1 wherein the fluid in the second phase is delivered in a volume of up to 200 ml per patient.

19. The method of claim 1 wherein the fluid in the second phase is delivered in a volume of up to 150 ml per patient.

20. The method of claim 1 wherein the flow injection rate of the first phase is equal to or greater than the injection flow rate of the second phase.

21. The method of claim 1 wherein the flow injection rate of the third phase is equal to or greater than the injection flow rate of the second phase.

22. The method of claim 1 wherein the first concentration and the third concentration are approximately equal.

23. The method of claim 1 wherein the fluid in the first phase and the fluid in the third phase are delivered from a first source and the fluid in the second phase is delivered from a second source.

24. The method of claim 1 wherein a first source of a diluent fluid is provided and a second source of a second fluid having a concentration of contrast agent is provided, the fluid in the first phase being formed by mixing the diluent fluid and the second fluid and the fluid in the third phase being formed by mixing the diluent fluid and the second fluid.

25. The method of claim 24 wherein the diluent fluid is water, physiological saline, an aqueous solution of at least one blood expander or pharmaceutical excipients.

26. The method of claim 24 wherein the fluid in the second phase is formed by mixing the diluent fluid and the second fluid.

27. The method of claim 1 wherein the contrast agent includes at least one of Br, Zr, Te, I, La, Ce, Pr, Nd, Sm, Eu, Gd, Tb, Dy, Ho, Er, Tm, Yb, Lu, Pt, Au, Hg, Pb and Bi.

28. The method of claim 1 wherein the contrast agent comprises at least one of an iodine containing monomer, an iodine containing dimer, a gadolinium containing monomer, a gadolinium containing dimer or a gadolinium containing oligomer.

29. The method of claim 28 wherein the contrast is ionic or nonionic.

30. The method of claim 1 wherein the fluid in the second phase is hyperosmolar with respect to blood.

31. The method of claim 1 wherein the contrast agent includes more than one contrast enhancing element.

32. The method of claim 1 wherein the contrast agent comprises at least one contrast enhancing element selected from an iodine-containing monomer, an iodine-containing dimer, a gadolinium-containing monomer, a gadolinium-containing dimer, and a gadolinium-containing oligomer.

33. The method of claim 1 wherein contrast agent in the first phase is of a different composition than the composition of contrast agent of the second phase or of the composition of contrast agent of the third phase.

34. The method of claim 1 wherein contrast agent in the third phase is of a different composition than contrast agent of the second phase or of a different composition than contrast agent of the first phase.

35. The method of claim 1 wherein the osmolarity of the first phase is within 20% of the osmolarity of the patient's blood.

36. The method of claim 1 wherein the osmolarity of the first phase is within 10% of the osmolarity of the patient's blood.

37. The method of claim 9 wherein the osmolarity of the third phase is within 20% of the osmolarity of the patient's blood.

38. The method of claim 9, wherein the osmolarity of the third phase is within 10% of the osmolarity of the patient's blood.

* * * * *